United States Patent [19]

Hilal et al.

[11] Patent Number: 5,127,626
[45] Date of Patent: Jul. 7, 1992

[54] APPARATUS FOR SEALING AROUND MEMBERS EXTENDING THERETHROUGH

[75] Inventors: Said S. Hilal, Laguna Niguel; Robert P. Cooper, Yorba Linda; Donald L. Gadberry, Huntington Beach, all of Calif.

[73] Assignee: Applied Vascular Devices, Inc., Laguna Hills, Calif.

[21] Appl. No.: 590,181

[22] Filed: Oct. 2, 1990

Related U.S. Application Data

[63] Continuation-in-part of Ser. No. 429,854, Oct. 31, 1989, abandoned.

[51] Int. Cl.⁵ .................... F16L 37/28; A61M 5/178
[52] U.S. Cl. .................... 251/149.1; 251/7; 251/251; 604/167; 604/256; 604/905
[58] Field of Search .......... 251/7, 8, 251, 167, 251/149.1; 604/34, 256, 905

[56] References Cited

U.S. PATENT DOCUMENTS

| | | | |
|---|---|---|---|
| 729,423 | 5/1903 | Scheiber et al. | 251/7 |
| 3,086,797 | 4/1963 | Webb | 251/7 |
| 3,197,173 | 7/1965 | Taubenheim | 251/7 |
| 3,438,607 | 4/1969 | Williams et al. | 604/34 |
| 3,920,215 | 11/1975 | Knauf | 251/7 |
| 3,977,400 | 8/1976 | Moorhead | 128/214.4 |
| 4,149,535 | 4/1979 | Volder | 128/214.4 |
| 4,231,400 | 11/1980 | Friedling | 137/798 |
| 4,243,034 | 1/1981 | Brandt | 128/221 |
| 4,324,239 | 4/1982 | Gordon et al. | 604/256 |
| 4,378,013 | 3/1983 | LeFevre | 251/7 |
| 4,473,369 | 9/1984 | Lueders et al. | 604/905 |
| 4,496,348 | 1/1985 | Genese et al. | 604/167 |
| 4,634,421 | 1/1987 | Hegermann | 604/34 |
| 4,723,550 | 2/1988 | Bales | 128/344 |
| 4,786,028 | 11/1988 | Hammond | 251/7 |
| 4,839,471 | 6/1989 | Clark | 277/192 |
| 4,960,259 | 10/1990 | Sunnanväder et al. | 251/7 |
| 4,978,341 | 12/1990 | Niederhauser | 604/167 |
| 5,009,643 | 4/1991 | Reich et al. | 604/167 |

FOREIGN PATENT DOCUMENTS 1023320  3/1953  France ..................... 251/8

Primary Examiner—A. Michael Chambers
Attorney, Agent, or Firm—Richard L. Myers

[57] ABSTRACT

An apparatus is provided for sealing around shafts or tubes of varying diameter. Its basic element comprises an elastomeric sealing body with an axial passage which is radially compressed from more than two sides to compress the passage into sealing engagement with a member extending through the passage. Radial compression is achieved by cams and followers disposed around the body which cooperate with angularly spaced radially extending lugs formed integrally with the body. The cams are spring biased to normally compress the axial passage of the sealing body. Levers operable by one hand of the user are provided to selectively release the apparatus.

11 Claims, 3 Drawing Sheets

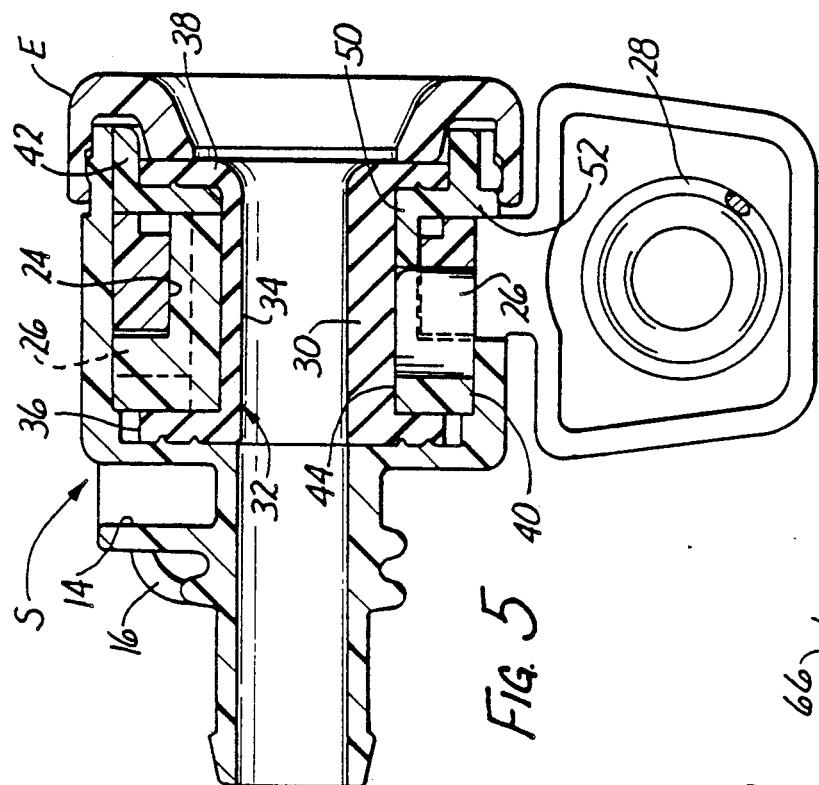
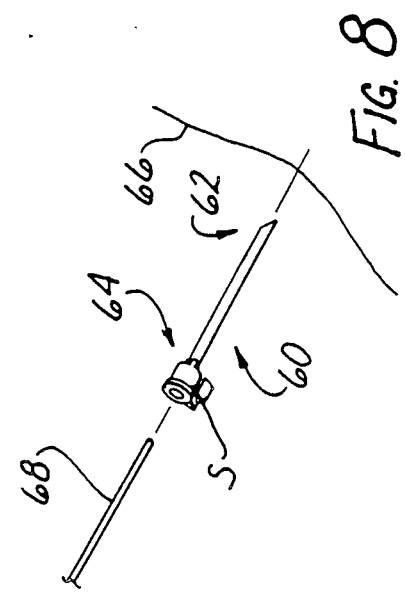
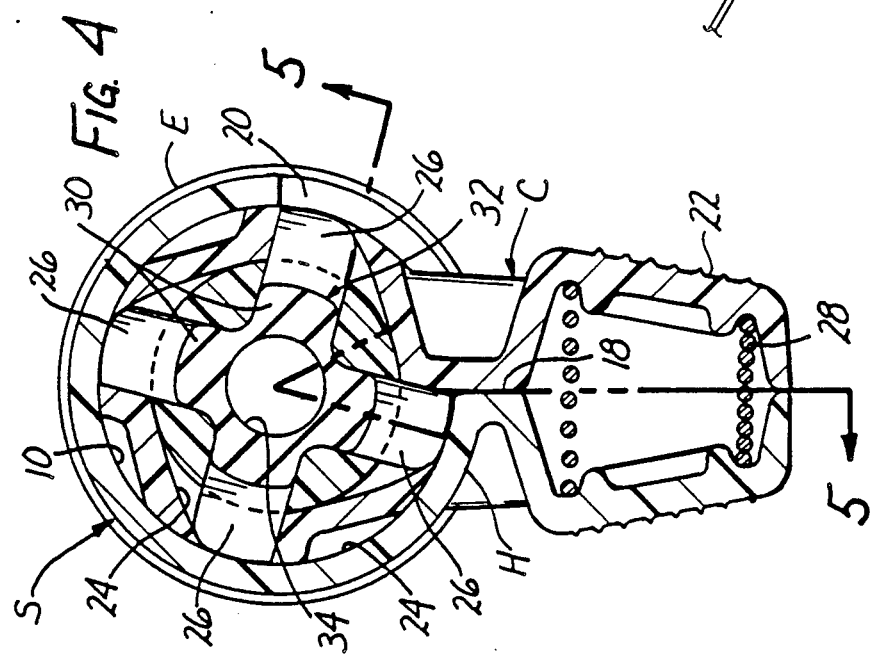

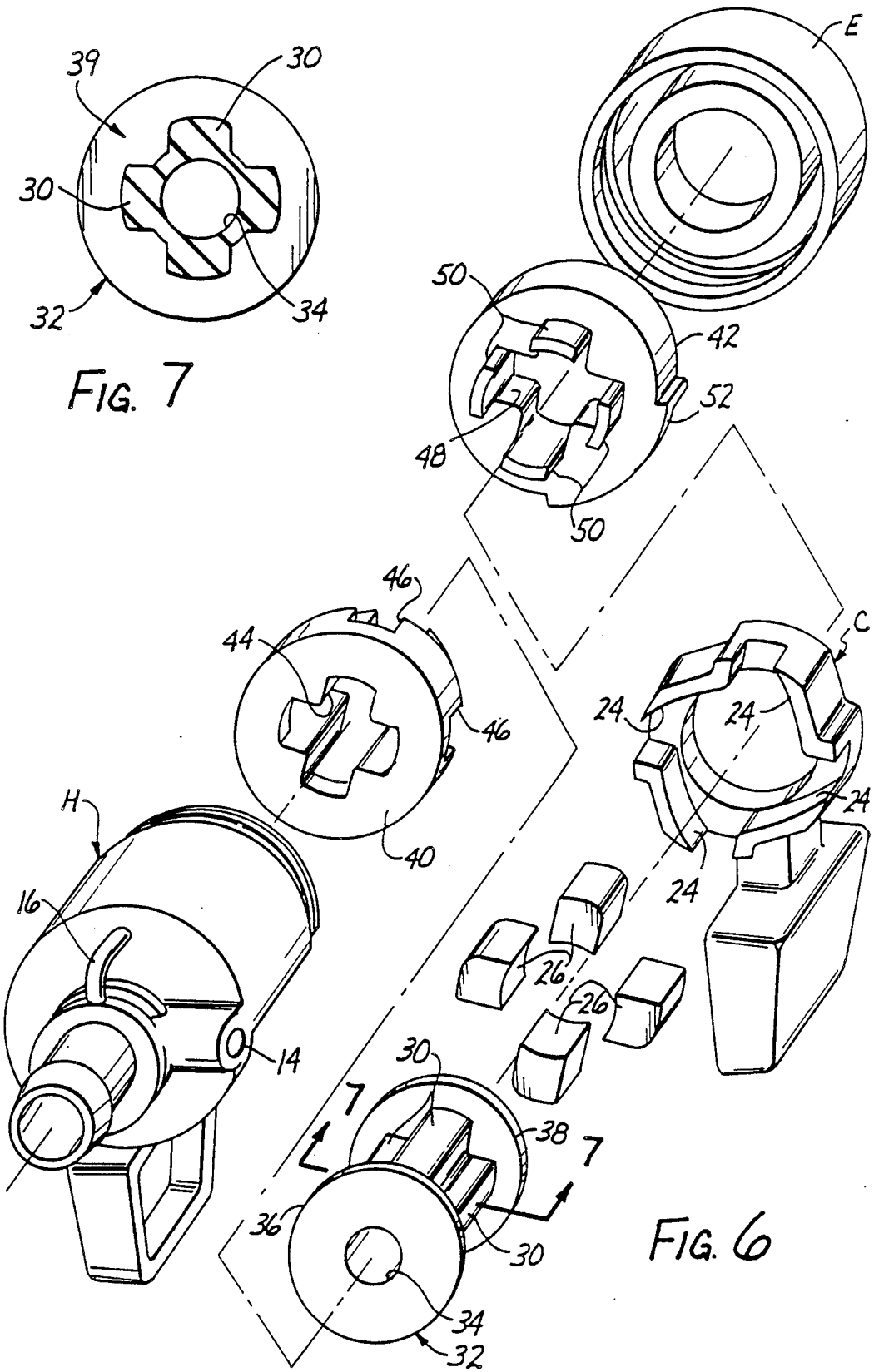

APPARATUS FOR SEALING AROUND MEMBERS EXTENDING THERETHROUGH

BACKGROUND OF THE INVENTION

REFERENCE TO RELATED APPLICATIONS

This is a continuation-in-part of U.S. patent application, Ser. No. 429,854, filed on Oct. 31, 1989, now abandoned, the filing date of which is hereby claimed for common subject matter under the terms of 35 U.S.C. 120.

FIELD OF THE INVENTION

The present invention relates generally to an improved device for forming a seal around shafts or tubes and, more specifically, to a hemostasis valve for sealing around elongate objects of varying sizes.

DISCUSSION OF THE PRIOR ART

Historically, seals and seal materials have been selected from materials having a high modulus. The theory was that a seal must fill a gap between two objects, thus permitting no gas or fluid to find or generate a path around the object. It was thought that if the seal material had a low modulus, such a path would form. Accordingly, seals designed for retaining pressure were deliberately manufactured out of high modulus materials. As a consequence, the seals had little or no compliance or conformance to accommodate variations in the shape of an object around which a seal was required. O-rings, for example, accommodate one external and one internal diameter, with slight allowances for manufacturing tolerances of the shaft or gland. If deviations from the tolerances are encountered, or if the shaft or gland is out of round, the O-ring is likely to fail or leak unless a deforming compressive force is applied to the O-ring to cause it to come into closer contact with the shaft or gland wall.

The latter approach creates significant problems, not the least of which is the limits it places on the range of deformation. A major drawback associated with the seal materials of the past has been the compressive force that the O-ring or seal transmits to the traversing shaft, especially if the shaft is of a fragile nature. Seals having a high modulus also fail to work if the traversing shaft is not relatively round, or if there are more than one traversing shaft extending through the seal at the same time.

Other types of seals used in the medical field are the "septum" and "duck-bill" seal. While satisfactory for certain limited purposes, these seals do not provide the advantages of the present invention.

In the septum seal, a septum or diaphragm is used as the sealing element. In order to transverse the seal, a preformed puncture is provided or a needle is used to generate a puncture within the septum and the traversing shaft is introduced into this puncture. Puncturing the septum is an added step that is often disliked in busy clinical settings. Finding the puncture hole is also difficult, particularly where lighting is sparse. The introduction of new shafts may require new punctures. This type of seal also fails to provide for locking the traversing shaft in place. These deficiencies of the septum seal have become well known so that it is now customary to provide more than one such seal in series.

The duck-bill seal is commonly used as a one way valve. It consists of a circular passage that flattens towards the tip, forming an area where two surfaces co-act to seal flow from outside the valve. The seal is effective around a shaft only so long as the pressure causing closure of the seal is sufficiently large. It is very difficult to purge air bubbles out of a valve incorporating a duck-bill seal. Such seals also have difficulty in sealing around a traversing shaft of an irregular shape. The shape of the seal which forms around a traversing shaft is commonly referred to as the "cat-eye" and permits leakage at two opposing points along the shaft. A duck-bill seal also tends to invert when a bulky shaft is pulled back through it.

The prior art also suggests deflectable tubular elements which are deformed to effect a seal. U.S. Pat. Nos. 3,977,400 and 4,243,034 teach such arrangements where the tubular elements are clamped from opposite sides by cam-like actuators. In both of these patents, the clamping is effected from two sides only. U.S. Pat. No. 3,970,089 teaches an arrangement wherein the tubular element takes the form of a toroid which is inflated to effect a seal. U.S. Pat. No. 4,580,573 teaches an arrangement wherein the tubular element is twisted to effect the seal.

The prior art also teaches stoppers for ampoules and the like wherein the stopper takes the form of an elastomeric member having a preformed opening which may be pinched shut. U.S. Pat. No. 2,797,837 discloses such a device. As shown in that patent, pinching is effected by either biasing the opening from one side, or clamping it from opposite sides.

SUMMARY OF THE INVENTION

In the apparatus of the present invention, an elastomeric sealing body having a passage extending axially therethrough is radially clamped from more than two sides. The preferred embodiment employs a sealing body having radially extending lugs disposed at substantially equal angularly spaced locations therearound and a clamp disposed at least partially around the sealing body to compress the lugs. The preferred embodiment also includes biasing means associated with the clamp to normally compress the sealing body and release means operable by one hand of a human operator to selectively release the sealing body from compression by the biasing means.

In accordance with one aspect of the invention, a seal assembly includes an elastomeric element defining an opening adapted to receive a shaft having a cross-sectional dimension and an outer surface. The assembly also includes means for compressing the element against the outer surface of the shaft to form with the shaft a seal having a particular area. Means is provided for applying a force to the element to produce a pressure on the particular area, the magnitude of the applied force being variable directly with the size of the particular area. In this aspect of the invention, the pressure on the particular area tends to be independent of the cross-sectional dimension of the shaft. In a particular embodiment the force applying means includes more than two dogs movable radially to produce the applied force. Means can be provided for biasing the opening of the elastomeric element toward a decreasing dimension.

In another aspect of the invention, a seal assembly includes a housing with two portions which are movable relative to each other. A compressive element is disposed in the housing and adapted to form a seal with an object, the element having properties responsive to an applied force to create a resultant force on the object. The two housing portions are movable relative to each other to vary the applied force on the compressive element and the resultant force on the object. The compressive element has properties such that the resultant force is greater than 80% of the applied force so that very little energy is lost in compressing the element. First and second opposed surfaces are associated with the respective portions of the housing and support opposite ends of a spring which biases the housing to decompress the seal element.

In still a further aspect of the invention, a seal material disposed in the housing has an outer surface and an inner surface which defines a central bore adapted to receive the object. Pressurizing means is disposed to exert an applied pressure from more than two directions against the outer surface of the seal material. By operation of the pressurizing means, the seal material produces a resultant pressure on the object thereby creating a seal. In a particular embodiment the seal material is provided with four projections which extend radially in cross-section to form the configuration of a cross.

The concept of this invention is particularly useful in combination with an access device adapted to be percutaneously inserted to provide an access channel into the body of a patient, the channel being adapted to receive an elongate object extending through the access device. An elongate tube includes a distal end and a proximal end, and portions defining the access channel along a longitudinal axis of the tube. Sealing means is disposed in proximity to the proximal end of the elongate tube for sealing the access device around the object. A seal material included in the sealing means is movable radially of the tube to form the seal between the tube portions and the elongate object.

It follows from these different aspects, that a principal object of the invention is to provide a seal that facilitates gentle sealing around shafts and tubes of varying diameters.

Another object is to provide such a seal capable of conforming to objects of irregular shape and/or simultaneously sealing around more than one object extending through the seal.

A further object of the invention is to provide such a seal which functions to axially retain an element extended therethrough.

An additional object of the invention is to provide an atraumatic seal which produces a substantially constant low pressure on the fragile wall of an object regardless of the cross-sectional dimension of the object.

Still another object of the invention is to provide such a seal which normally assumes a closed condition and may be operated and selectively released by one hand of a human operator.

The foregoing and other objects will become more apparent when viewed in light of the and following detailed description and reference to the associated drawings.

BRIEF DESCRIPTION OF THE DRAWINGS

FIG. 4 is a cross-sectional view similar to FIG. 2, showing the apparatus with the sealing member in the open condition;

FIG. 5 is a cross-sectional view taken on the plane designated by line 5—5 of FIG. 4; and FIG. 6 is an exploded perspective view of the apparatus.

FIG. 7 is a cross-sectional view of a particular embodiment of the sealing member taken along lines 7—7 of FIG. 6; and FIG. 8 is a perspective view of a medical access device with the sealing apparatus of the present invention disposed at the proximal end of the device.

DESCRIPTION OF THE PREFERRED EMBODIMENTS

Figure 1:
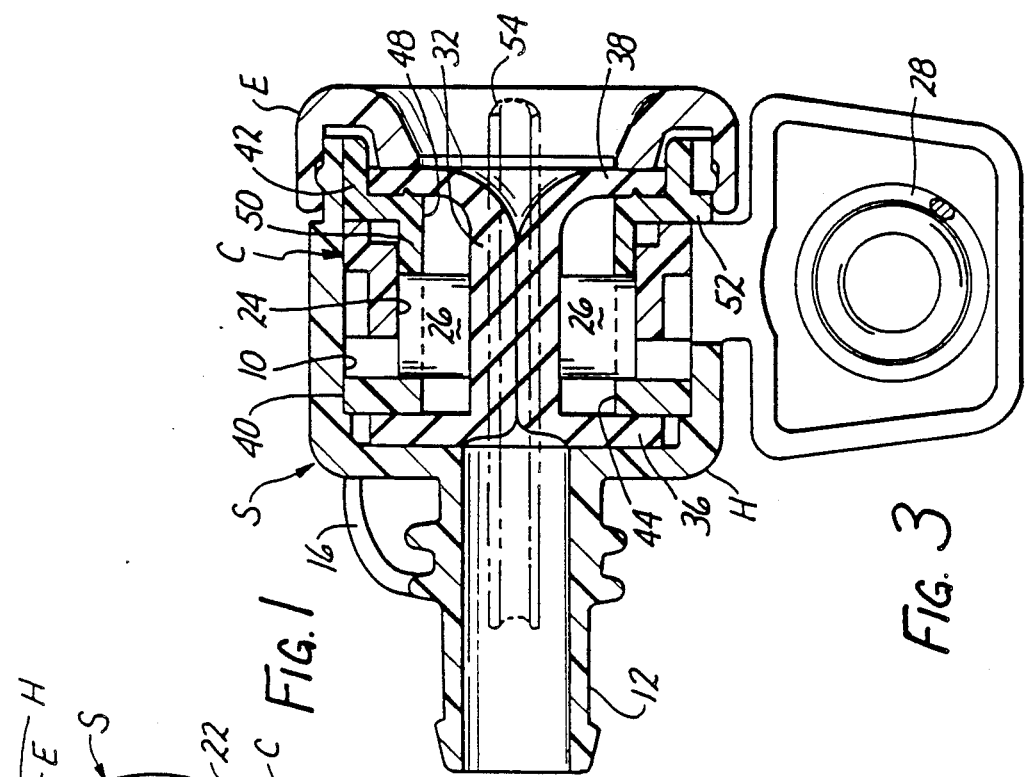
FIG. 1 is a perspective view of the apparatus.

The sealing apparatus is designated in its entirety by the letter "S" and comprises, as its basic element: a housing body "H", a cam body "C" and an end cap "E". The housing Body "H" includes an enlarged open-ended cavity 10 having a tubular conduit fitting 12 communicating therewith. In a preferred embodiment, a side port 14 is formed in the body "H" and communicates with the interior of the fitting 12. A suture loop 16 is formed integrally with the housing and connects to the fitting 12. A stationary lever 18 is formed integrally with and extends laterally of the housing body "H". An elongate arcuate slot 20 extends through the housing body "H" to one side of the lever 18 for accommodation of a cam lever 22 forming part of the cam body "C". The slot opens through one end of the body "H" to facilitate assembly of the apparatus.

Figure 2:
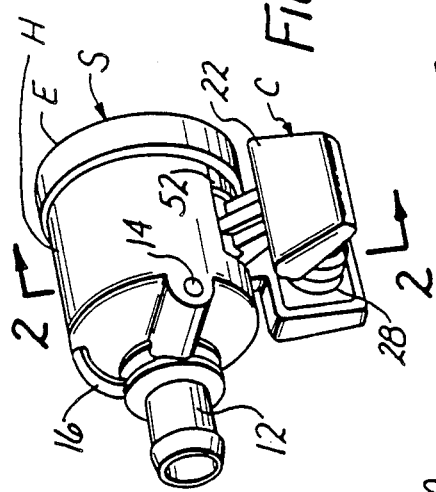
FIG. 2 is a cross-sectional view taken on the plane designated by line 2—2 of FIG. 1, showing the apparatus with the sealing member in the normally closed condition.

In the assembled condition, the cam body "C" is concentrically received within the housing body "H", with the lever 22 extending through the slot 20. The exterior surfaces of the cam body are of an arcuate configuration and configured to slide on the interior surface of the cavity 10 (see FIGS. 2 and 4). Interiorally, the cam body "C" is formed with four cam surfaces 24. The cam surfaces are associated a plurality of pawls or cam follower pins 26 which are spaced relative to one another by a distance approximately equal to the width of the pins. As viewed in FIGS. 2 and 4, counterclockwise movement of the cam body "C" relative to the housing body "H" functions to force the pins 26 inwardly to the position shown in FIG. 2. Clockwise movement functions to release the pins for extension, as shown in FIG. 4. A compression coil spring 28 is engaged between the levers 18 and 22 to normally bias the lever 22 in the counterclockwise direction, toward an inwardly position as shown in FIG. 2.

The pins 26 engage lugs 30 formed on an elastomeric sealing member 32. This sealing member 32, which is best illustrated in FIG. 6, includes a central section 33 which extends longitudinally of the sealing member 32 between a pair of annular end flanges 36 and 38. Portions of the central section 33 and the end flanges 36, 38 define a central bore or passage 34 which extends axially through the sealing member 32 in a preferred embodiment.

The lugs 30 extend longitudinally of the sealing member 32 between the end flanges 36, 38. These lugs 30 are formed by removing material or longitudinal cut-outs from the exterior surface of the central section 33. In FIG. 6, one of these cut-outs is shown generally at the arrow 39.

As illustrated in the cross-section of FIG. 7, the sealing element 32 can have a plurality of the lugs 30 angularly spaced around the bore 34. In the illustrated embodiment each of the lugs is defined by a width which is approximately the diameter of the bore 34. Each of the longitudinal cut-outs, illustrated by the arrow 39, is defined by an adjacent pair of the lugs 30. In a preferred embodiment, the sealing member 32 includes four radially extending lugs 30 equally spaced at ninety degree intervals around the bore 34. This provides the sealing member 32 with a central portion 33 which in radial cross-section appears to have the configuration of a cross.

The material associated with at least the central portion 33 of the sealing member 32 is of particular interest to the present invention. This material is preferably very soft and pliable so that a pressure applied to the sealing member 32 will force the central section 33 into the regions defining the bore 34. With an appropriate material, this pressure on the sealing element 32 will force it into contact with any object, such as a catheter or surgical instrument, extending through the bore 34. In this manner the sealing element 32 tends to form a seal with the exterior surface of any such object or objects.

If the material is appropriately selected, the member 32 can form a seal even around objects or shafts which have irregular cross-sectional configurations. Such an object may include a single shaft having an irregular configuration or multiple shafts each of which has a regular configuration.

The material of at least the central section 33 of the sealing member 32 preferably has a Shore A hardness less than twenty (20). A material with this degree of softness will tend to function with characteristics similar to that of a fluid. Thus the pressure applied to the outer surface of the central portion 33 will be transmitted with very little loss of energy to the portions defining the bore 34. It follows that any energy required to deform such a material can be minimized. A soft material is also similar to a fluid in that it is highly compliant so that it can "flow" into narrow crevices as might be required to form a tight seal around an irregular shaft or object. A soft material with these significant fluid properties can be chosen to effect a high degree of conformity to any shape of object extending through the bore 34.

Another fluid characteristic associated with the material of the sealing member 32 is the property it has for transferring substantially all of the applied force to the region defining the bore 34. Thus, a pressure applied by the cam follower pins 26 to the lugs 30 is substantially the same pressure exerted by the portions defining the bore 34 against an object extending through the bore. With a material of low durometer, very little energy is lost in deforming the sealing member 32. In fact, a suitable material is substantially non-compressible so that the resultant pressure at the bore 34 is at least eighty percent (80%) of the pressure applied to the lugs 30.

Under particular circumstances, it may be desirable that the material forming the bore 34 have particular surface characteristics. In some cases, a degree of impermeability may be required. In other cases, a high or low coefficient of friction may be desired to either facilitate axial movement or prevent axial movement of the object respectively. These characteristics can be provided in at least two manners. In the first case, the material forming the sealing member 32 can be chosen with homogeneous properties which can provide the surface characteristics desired. Thus a hydromer material can be incorporated into an elastomer to provide a lubricous surface defining the bore 34. In other cases, a coating can be applied to the portions defining the bore 34. This coating might include polytetrafloroethylene when a biocompatible surface is desired. Suitable coatings can be grafted or otherwise bonded to provide a lubricous surface. By way of example, a hydromer or hydrogel coating might provide the surface of the bore with a coefficient of friction less than 0.25.

In a preferred embodiment, the material selected for the sealing member 32 is silicone rubber. This material has a Shore A hardness less than twenty (20) and can be molded to a monolithic construction including not only the central portions 33 but also the flanges 36 and 38. It has been demonstrated that materials exhibiting a Shore A hardness as low as five (5) are suitable for application to this concept. The material forming the seal member 34 preferably has compression characteristics defined by a Poisson's Ratio in a range between 0.45 and 0.50.

In another embodiment, the central portions 33 of the sealing member 32 are formed from foam rubber. This material can also be configured to provide a very low Shore hardness factor such as twenty (20) or even lower. In a preferred embodiment, foam rubber is extruded to form the central portions 33, and the end flanges 36 and 38 (which may be formed from a non-foam material) are glued or otherwise attached to extend radially from the ends of the central portion 33.

In a particular application, foam rubber may be particularly advantageous for the sealing member 32. The rubber forming the foam will typically be stronger than a homogeneous material so it will tend to resist tearing and propagation of cracks. It is the dispersion of a multiplicity of air holes in this foam which can provide the stronger rubber material with the soft compression characteristics previously discussed.

If the material forming the sealing member 32 is constructed of foam, it may be desirable to remove the foam "skin" which is typical of this material. Such a skin may tend to interfere with the compression characteristics of the sealing member 32 or otherwise impair the ability of the material to conform to an irregularly shaped object.

Before being assembled into the housing body "H", a retainer ring 40 and a spacer ring 42 are engaged around the sealing member 32. Both of these rings have arcuate outer surfaces designed to complimentally engage the interior surface of the recess 10. A cross-shaped passage 44 is formed in the ring 40 for receipt around the lugs 30 of the sealing member. The opening 46 shown by the arrow 39 extend radially through the ring 40 in alignment with the lug receiving recesses of the passage 44. These openings 46 as will become more apparent from the subsequent discussion, slidably receive the pins 26.

The spacer ring 42 is formed with a cross-shaped passage 48 adapted to be received around the lugs 30 of the sealing member 32. Fingers 50 extend from the distal ends of the passage 48 in a longitudinal direction relative to the ring 42. These fingers, together with the recesses 46, provide radial passages for slidable receipt of the pins 26. An arcuate segment 52 is formed on the outside of the spacer ring 42 for engagement in the slot 20 to locate the fingers 50 and pins 26 relative to the cam body "C".

Referring again to the material forming the sealing member 32, it will be apparent that any material having a low durometer, must be confined in order that a pressure applied to the material will force it into the desired region such as the bore 34. In the illustrated embodiment the housing H and end cap E, as well as the retainer ring 40 and spacer ring 42 provide the confining means and are configured to define a cavity similar in shape to the exterior surface of the sealing member 32. Then as the cam follower pins 26 are moved radially against the lugs 30 of the sealing member 32, this pressure forces the material of the central portions 33 into the region of the bore 34.

Prior to being inserted into the housing body "H", the rings 40 and 42 and the cam body "C", with the pins 26 in place, are assembled around the sealing member 32. During this assembly, flanges 36, 38 of the sealing member 32 can be resiliently deflected to pass through the various elements. The arrangement of this subassembly can be seen from the center line extending through the exploded view of FIG. 6.

Figure 3:
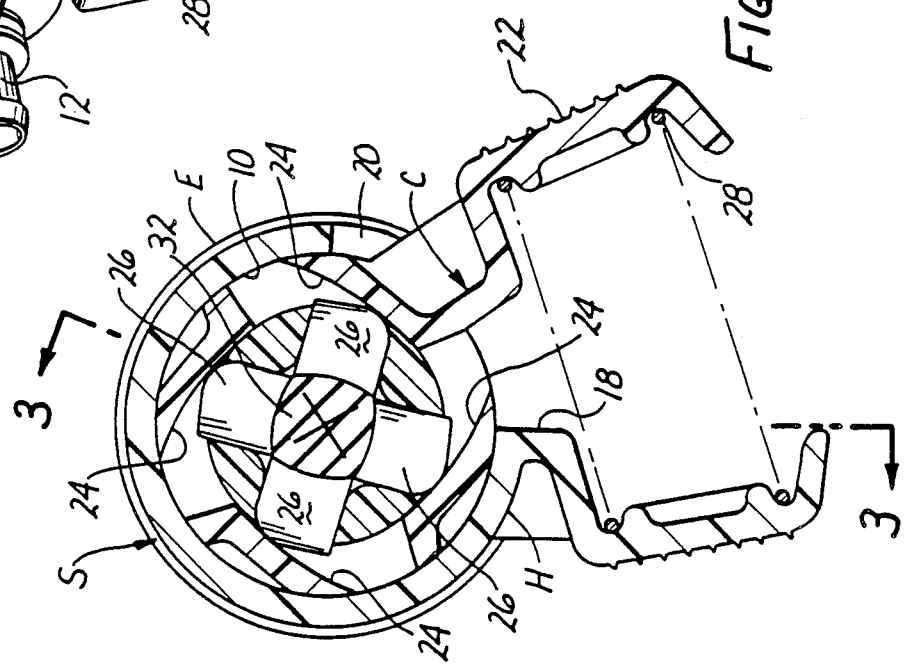
FIG. 3 is a cross-sectional view taken on the plane designated by line 3—3 of FIG. 2.

The assembly of the sealing member 32, rings 40 and 42, cam body "C" and pins 26 creates a subassembly which is then slid into the housing body "H" so as to engage the segment 52 in the slot 20 and position the cam lever 22 in apposition to the stationary lever 18. The end cap "E" is then snapped into place, as seen in FIGS. 3 and 5. The arcuate segment 52 serves to lock the spacer ring 42 against rotation relative to the housing body "H". This, in turn, locks the sealing member 32 and the retainer ring 40 against rotation relative to the housing, while leaving the cam body "C" free for rotation about the longitudinal axis of the housing body. After the stationary lever 18 and cam lever 22 are disposed in apposition, the compression coil spring 28 is interposed therebetween, thus forcing the levers apart and moving the pins inwardly, as shown in FIG. 2.

The surface on the stationary lever 18 and the surface on the cam lever 22, both of which contact the spring 28, are angularly disposed with respect to each other. In a preferred embodiment, each of these surfaces is disposed in a plane which is generally parallel to the axis of the bore 34. As these surfaces are moved toward each other, the spring 28 is compressed and tends to exert a force which increases as the spring 28 is compressed. As the spring 28 is permitted to relax, these two opposing surfaces separate angularly and the force of the spring 28 tends to decrease. It will be apparent that the spring 28 can be chosen with a spring constant which is suitable to provide a particular sealing pressure for a specific application.

It is of particular advantage that the force applied to the lugs 30 of the sealing member 32 be directed radially of the bore 34. This tends to insure that the material of the sealing member 32 is pushed most directly to fill the space of the bore 34. By guiding the cam follower pins 26 radially, the fingers 50 together with the recesses 46 provide means for translating the rotational movement of the cam surface 24 into a radial, linear movement of the cam follower pins 26.

It is believed to be important that the force applied against the sealing member 32 be directed from more than two radial directions. Only with the application of an applied force from three or more radial directions, can one avoid the cat-eye which is typical of the seals of the prior art. The conformity of the sealing member 32 to irregularly shaped objects extending through the bore 34 is greatly increased by the provision of four of the lugs 30 in the preferred embodiment. Particularly large diameters of the bore 34 may be accommodated with more than four of the lugs 30. With a radial force applied along each of these lugs 30 the material tends to flow with little pressure into the region of the bore 34 thereby creating a compliant seal with any shaft or object extending through the bore 34.

The compression spring 38 is of significant interest to the present invention as it provides means for biasing the sealing member 32 against any object extending through the bore 34. If there is no such object, the spring will bias the sealing member 32 to entirely close the bore 34. Thus the sealing member 32 can close to a diameter of zero (0), that is to say it can actually form a seal against itself. This is certainly one of the most significant advantages associated with the present invention as it permits objects to be entirely removed from the bore 34 without permitting a loss of gas pressure or liquids which might otherwise past through the unoccupied bore 34. At the same time, resistance applied against the compression spring 28 can open the bore to significant diameters such as sixty French (60 Fr.) to permit the insertion of objects with substantially no frictional resistance from the sealing member 32. Then by releasing pressure on the spring 28, the sealing member 32 can close against the exterior surface of the object to again seal the bore 34.

The range of sealing diameters which can be achieved with this concept are indeed significant in view of prior art grommets and seals which were generally incompetent for forming seals over a range of more than fourteen French (14 Fr.). The punctured or slit septums of the prior art which were the only seals that could provide for closure against themselves, generally leaked with diameters greater than eleven French (11 Fr.). Thus seals which could achieve zero diameter could accommodate a range of only eleven French (11 Fr.).

Another feature associated with the present invention related to the amount of pressure which is exerted on an object extending through the bore 34. In some cases these objects are quite fragile. For example, a catheter is typically constructed with a thin wall so that significant forces on the catheter can actually result in occluding the lumens or otherwise impacting the performance of the catheter. Fragile optical fibers can also be easily broken with septum seals and elevated sealing pressures. With the present invention, this sealing pressure can not only be limited but can be carefully controlled. This is due to some extent to the nature of the material forming the sealing member 32. With the significant fluid characteristics previously discussed, the pressure applied to the material 34 is substantially equal to the resultant pressure applied by the material 32 against the object.

In spite of the fact that a spring is used to create the applied force, and a spring tends to exhibit a greater force when compressed than when relaxed, the pressure created by the material 32 against an object can be maintained generally constant. Thus regardless of the cross-sectional dimension of the object, the pressure exerted to form the seal need not vary significantly. This is true regardless of the surface area of the seal because the highest spring force is applied to the seal material 32 when the bore has its largest diameter. Thus the spring exerts a force which in general is directly proportional to the area of the seal. Where that area is formed against a larger diameter object, the force is increased so that the pressure against the greater surface area remains substantially constant. Thus the spring 28 provides means for biasing the sealing member 32 with a decreasing force toward a decreasing bore dimension.

The sealing assembly associated with the present invention is particularly advantageous when used in combination with access devices. These devices commonly vascular introducers, surgical trocars, and other cannula which provide percutaneous access to the body of a patient. In these environments, the access channel provided by the access device can be sealed by the seal assembly to inhibit any loss of fluid. This fluid may be gas which is used to achieve pneumoperitoneum in a laproscopic procedure. It may also include body fluids such as blood in the case of a vascular access device such as an introducer.

An exemplary access device is illustrated in FIG. 8 and is designated generally by the reference numeral 60. This device could, for example, be either an introducer or a surgical trocar which typically includes a distal end 62 and a proximal end 64. The seal assembly S is preferably mounted at the proximal end 64 of the device and remains exterior of the patient after the distal end 62 of the device 60 is introduced percutaneously of the skin 66 of the patient. In this manner, the seal assembly S provides means for sealing a working channel or bore of the access device 60 around objects such as catheters and instruments, collectively designated by the reference numeral 68, which are operatively inserted through the working channel of the device 60.

OPERATION

Once the sealing apparatus is assembled, its operation is very simple. To condition the apparatus for passage of an element therethrough, it is simply necessary to squeeze the levers 18 and 22 together, thus opening the passage 34 as shown in FIG. 4. The element may then be freely extend through the passage. Upon being positioned as desired, the levers 18 and 22 are released, thus closing the passage into sealed engagement with the element. The latter operation also functions to grip the element and hold it at the desired location. Release of the element is achieved by simply again squeezing the levers 18 and 22 together against the biasing force of the spring 28.

It should be appreciated that the solid line representations shown in FIG. 2 and 3 illustrate the sealing member in the fully closed condition, without an elongate element extending therethrough. This is intended to demonstrate that the apparatus will provide a seal, even in the absence of an element extending therethrough. The phantom lines shown in FIG. 3 illustrate how the sealing element accommodates an elongate element 54 extended therethrough.

CONCLUSION

From the foregoing detailed description, it will be apparent that the present invention provides an apparatus for sealing around elongate elements of various sizes and shapes, which apparatus may be operated with ease by one hand of the user. It should be appreciated, however, that the apparatus is not intended to be limited to the specifics of the illustrated embodiment, but rather is defined by the accompanying claims.

We claim:

1. An improved apparatus for sealing around a shaft or tube, said apparatus comprising:
   an elastomeric sealing body having a channel extending axially therethrough;
   a cage received around and extending axially of the body, said cage having more than two passages extending relative to the channel of the sealing body in angular relationship to one another;
   a follower slidably received in each of the passages of the cage and adapted for movement relative to the cage to radially compress the sealing body against and form a seal around the shaft or tube; and
   clamp means disposed at least partially around the cage for engaging the followers and radially compressing the sealing body into sealing engagement with the shaft or tube.

2. An apparatus according to claim 1 wherein the passages in the cage are disposed around the channel in the sealing body at substantially equally spaced angular intervals relative to one another.

3. An apparatus according to claims 1 and 2 wherein:
   the followers have portions extending outwardly from the cage; and
   the clamp means has cam surfaces engagable with said portions of the followers to force the followers radially inwardly along the passage of the cage.

4. An apparatus according to claim 1 or 2 wherein the sealing body has lugs extending into the radially extending passages of the cage.

5. An apparatus according to claim 1 or 2 further comprising biasing means operatively associated with the clamp means to normally compress the sealing body.

6. An apparatus according to claim 5 further comprising manual release means associated with the clamp means and operable by one hand of an operator to selectively release the sealing body from compression by the biasing means.

7. An apparatus according to claim 1 or 2 further comprising biasing means operatively associated with the clamp means to normally compress the sealing body.

8. An improved apparatus for sealing around a shaft or tube, said apparatus comprising:
   a housing;
   an elastomeric sealing body disposed in a housing and having a channel extending axially therethrough;
   a cage received around and extending axially of the body, said cage having more than two passages disposed around the channel in the sealing body at substantially equally spaced angular intervals;
   followers slidably received in the passages of the cage for movement relative to the cage to radially compress the sealing body against and form a seal around the shaft or tube;
   clamp means disposed in the housing at least partially around the cage for engaging the followers and radially compressing the sealing body into sealing engagement with the shaft or tube; and
   biasing means operatively associated with the clamp means for normally compressing the sealing body, the biasing means including a first lever fixed to and extending laterally from the housing, and a second lever operatively associated with the clamp means for movement relative to the housing, said second lever extending laterally from the housing in apposition to the first lever, and a spring disposed between the first and second levers to normally force the levers apart.

9. An apparatus according to claim 8 wherein the passages in the cage are more than two in number and are disposed around the channel in the sealing body at substantially equally spaced angular intervals.

10. An improved apparatus for sealing around shafts or tubes, said apparatus comprising:

a housing;

an elastomeric sealing body having a passage extending axially therethrough and with more than two radially extending lugs exposed at substantially equal angularly spaced locations around the body;

clamp means disposed in the housing at least partially around the sealing body, said clamp means being operable to radially compress the lugs to at least partially close the passage of the sealing body; and biasing means operatively associated with the clamp means to normally compress the sealing body, the biasing means including a first lever fixed to and extending laterally from the housing, a second lever operatively associated with the clamp means for movement relative to the housing, said second lever extending laterally from the housing in apposition to the first lever, and a spring disposed between the first and second levers to normally force the levers apart.

11. An apparatus according to claim 9 wherein the lugs are four in number and angularly spaced at 90 degree intervals around the sealing body.

* * * * *

UNITED STATES PATENT AND TRADEMARK OFFICE
CERTIFICATE OF CORRECTION

PATENT NO. : 5,127,626
DATED : July 7, 1992
INVENTOR(S) : Said S. Hilal, Robert P. Cooper, and Donald L. Gadberry It is certified that error appears in the above—identified patent and that said Letters Patent is hereby corrected as shown below:

Col. 4, line 5 delete the word "and"

Col. 10, line 18 delete the word "has" and add the word -- having --.

Signed and Sealed this

Twenty-first Day of September, 1993

Attest:

BRUCE LEHMAN

Attesting Officer         Commissioner of Patents and Trademarks